United States Patent
von Casimir

(10) Patent No.: US 6,755,806 B1
(45) Date of Patent: Jun. 29, 2004

(54) CATHETER INSERTION DEVICE WITH A SYSTEM FOR LIQUID-TIGHT CLAMPING OF THE INSERTION LUMEN

(76) Inventor: Wolf von Casimir, Kreuzeckstrasse 4, D-82327, Tutzing (DE)

( * ) Notice: Subject to any disclaimer, the term of this patent is extended or adjusted under 35 U.S.C. 154(b) by 0 days.

(21) Appl. No.: 09/424,898

(22) PCT Filed: May 28, 1998

(86) PCT No.: PCT/DE98/01466
§ 371 (c)(1), (2), (4) Date: Jan. 20, 2000

(87) PCT Pub. No.: WO98/53873
PCT Pub. Date: Dec. 3, 1998

(30) Foreign Application Priority Data

May 31, 1997 (DE) .......................... 197 22 753

(51) Int. Cl.[7] ..................... A61M 5/178; A61M 5/14
(52) U.S. Cl. .................. 604/167.03; 604/167.05; 604/256
(58) Field of Search ................. 604/523, 533–535, 604/539, 284, 513, 256, 167.01, 167.03, 167.05, 248, 537; 606/108

(56) References Cited

U.S. PATENT DOCUMENTS

| | | | |
|---|---|---|---|
| 4,726,374 A | * | 2/1988 | Bales et al. |
| 5,158,553 A | | 10/1992 | Berry et al. ............ 604/248 |
| 5,269,764 A | * | 12/1993 | Vetter et al. |
| 5,489,274 A | * | 2/1996 | Chu et al. |
| 5,700,251 A | * | 12/1997 | Miyauchi et al. ......... 604/264 |
| 5,935,112 A | * | 8/1999 | Stevens et al. |
| 6,165,168 A | * | 12/2000 | Russo |

FOREIGN PATENT DOCUMENTS

| | | |
|---|---|---|
| DE | 3324699 | 12/1984 |
| EP | 0455478 | 11/1991 |
| EP | 0546712 | 6/1993 |

* cited by examiner

Primary Examiner—Brian L. Casler
Assistant Examiner—Catherine S. Williams
(74) Attorney, Agent, or Firm—Milde & Hoffberg, LLP

(57) ABSTRACT

According to the invention, the lumen channel, which passes through a guide catheter and an insertion valve, said insertion valve being connected to said guide catheter, is also provided with a shut-off device at a certain point. Said shut-off device enables the lumen to be closed off by means of clamping. In the clamped position, the shut-off device therefore prevents blood from escaping from the insertion valve when it is necessary to open said insertion valve, for example, in order to introduce a treatment catheter.

13 Claims, 2 Drawing Sheets

CATHETER INSERTION DEVICE WITH A SYSTEM FOR LIQUID-TIGHT CLAMPING OF THE INSERTION LUMEN

BACKGROUND OF THE INVENTION

The invention has to do with an insertion system for use in entering the lumen of a blood vessel, to insert and replace treatment instruments.

Usually the Seldinger Technique is used for inserting catheters into blood vessels. By this means, an access called a hemostatic inserter projects out of the body surface. Its central opening is closed to begin with in self-acting fashion by means of a plug, made of soft elastic material in the shape of a star. Through this opening, the front end of a guide catheter is then extended into the lumen of the blood vessel until the tip of the guide catheter gets as close as possible to the treatment site with the actual treatment catheters or instruments. The back end of the guide catheter then lies outside the opening of the hemostatic inserter. An access is attached on this end of the guide catheter, to be closed by such means as a screw cap and to be opened partially or fully. This access is designated as an insertion valve.

The insertion valve is configured according to the packing box principle, and has a soft elastic, cylindrical sealing ring with a central opening. This sealing ring, depending on the desired sealing action or residual opening to be adjusted, is shape-adapted using an axially displaceable piston ring by compressing together.

One example of a task is to carry out coronary vessel dilation using a balloon dilation catheter, The task is to insert the guide wire and then the treatment catheter with its particular relatively sensitive tip into the lumen of the blood vessel so that it will not be damaged, and advance it to the location to be treated. To accomplish this, the access opening of the insertion valve must as a rule, be completely open. During the period until it can again be closed so that the guide wire or treatment catheter is tightly enclosed, but may simultaneously be able to be shifted longitudinally, several milliliters of surrounding blood of necessity is expelled.

As with the previously described insertion of the guide wire and the treatment catheter, these particulars essentially, including expelling of blood, are repeated in all additional measures for replacing the catheter, since the insertion valve must in each instance be opened for at least a few seconds. Overall blood loss in the course of such a treatment in this way can be considerable, especially in patients with high blood pressure. Contamination of the insertion valve's vicinity by blood has been assumed until now to be an unavoidable annoyance. Blood loss, if they are aware of it, can be perceived by patients to be psychologically stressful.

SUMMARY OF THE INVENTION

The invention solves the problem by improving and supplementing previous insertion systems so that all outflow of blood is avoided when using them.

The lockable insertion opening of the insertion valve with its sealing ring and the shutoff device somewhat carry out the function of two lock gates at the ends of a lock chamber in a channel which extends from the sealing ring into the lumen of the guide catheter. These functions can be taken over by the sealing ring and the shutoff device, if a guide wire is in the channel.

The invention-specific shutoff device, if brought into the closed setting, makes it possible at, at any time, to open the insertion valve without having blood come out of its central insertion opening. First, the guide wire, and next the catheter head, in the case, for example, of a balloon dilation catheter, with its tip and the dilation balloon, and at least one short part of the immediately adjoining catheter shaft, is pushed through the opened sealing ring of the insertion valve. As soon as this is done, the sealing ring, and thus its central insertion opening, without force or hurried activation, can be adapted to the diameter of the guide wire or of the catheter shaft. On the one hand, this achieves the necessary sealing action, and on the other, it permits the guide wire or catheter shaft to be moved longitudinally. If necessary, the guide wire which is laid before insertion of the catheter to the treatment site is held by the closed shutoff device, and is thus secured against being shifted longitudinally. By this means, the head of a following treatment catheter can be shifted from the end of the guide wire that lies outside, onto the guide wire, without this having to be separately held securely. After these steps, the shutoff device can be opened and the catheter head can be shifted in the direction of the treatment site.

DE-Cl-33 24 699 makes known a valve device in an aspirating set for carrying out central venous puncture, in the shape of a hose piece. Its internal cross section can be closed by twisting.

From EP-A2-0 546 712, a valve device for a so-called over-the-needle-in catheter, i.e., a short catheter is known which is to be placed as an access to a blood vessel by means of a puncture needed with its tip projecting out over its distal end. By means of a correcting element, the short catheter can be locked by pinching off at its proximal end.

Neither device makes provision, however, to create a lock chamber in the access area to the catheter by two lock gates, as is the case with the present invention.

One advantageous embodiment shape of an insertion system with the invention-specific shutoff device is characterized in having a side channel that empties at a suitable location, preferably in the area of the shutoff device, into the main channel. Through this side channel, a sterile, clear liquid, preferably physiological saline solution, can be injected into the lumen of the main channel between the emptying location and the sealing ring of the insertion valve. Use of a clear wall material in manufacturing at least the main channel between the shutoff device and the sealing ring makes it possible to observe the position of each catheter head during the insertion process. In other respects, the liquid is prevented from coming out of the insertion valve just as blood otherwise is. The liquid represents a "clean additive stopper" of the system. As a further improvement, an additional side channel is provided, for example as close as possible to the sealing ring, via which the liquid can be injected or changed without even partial opening of the insertion valve, if it should gradually become mixed with blood due to longitudinal shifting of the treatment catheter.

For a full understanding of the present invention, reference should now be made to the following detailed description of the preferred embodiments of the invention as illustrated in the accompanying drawings.

DESCRIPTION OF THE PREFERRED EMBODIMENTS

Figure 1A:
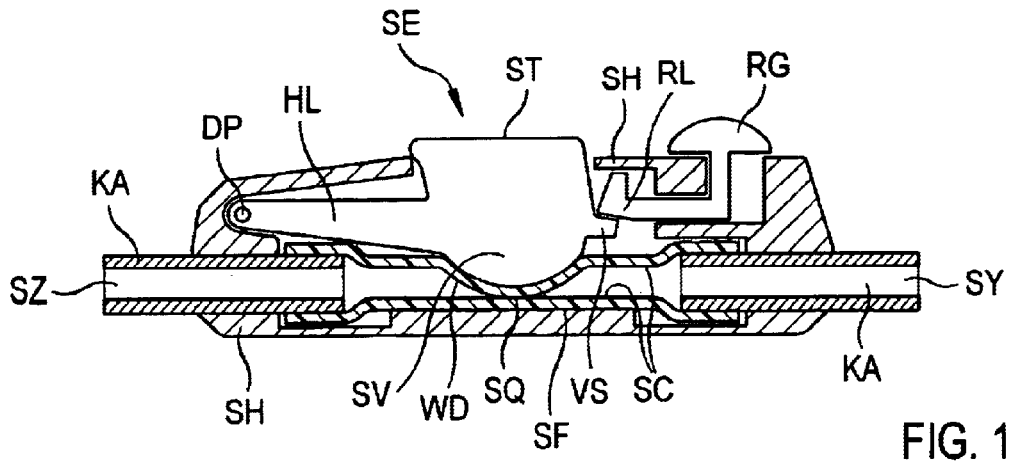
FIGS. 1a and 1b are schematic depictions of a shutoff device in its closed and open setting.

The preferred embodiments of the present invention will now be described with reference to FIGS. 1–3 of the drawings. Identical elements in the various figures are designated with the same reference numerals.

Figure 1B:
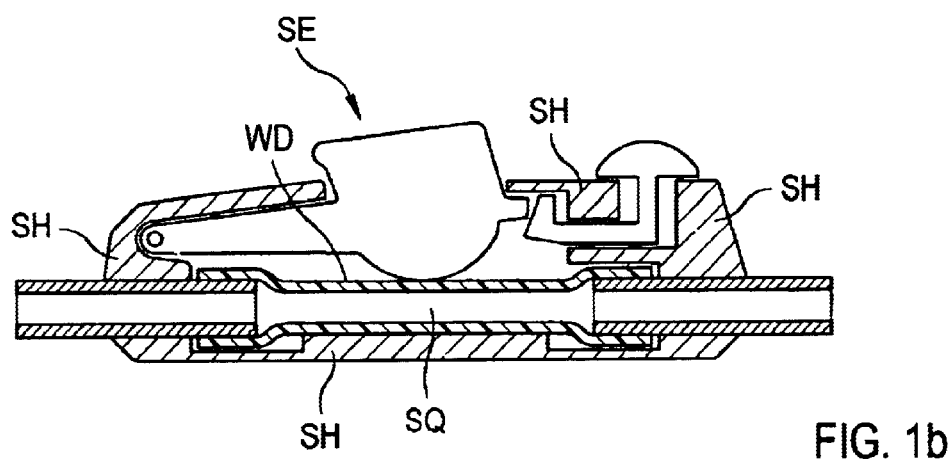

The shutoff device SE depicted in FIGS. 1a and 1b is configured according to the principle of a hose clamp. The two most essential pieces of shutoff device SE are the hose piece SC, which runs from an insertion valve EV to the channel KA that extends into guide catheter shaft FS; and adjusting device SV. Hose piece SC lies within the influence area of adjusting device SV on support surface SF, while adjusting device SV is attached to a lever HL, which is braced so as to swivel about fulcrum DP on shutoff device housing SH. By means of locking button ST, adjusting device SV can be compressed against hose piece SC until its internal cross section (clamping cross section SQ) is closed liquid-tight. In this closed setting, the adjusting device SV is held by a bolt RL which projects into the swivel zone of a projection VS on lever HL. If bolt RL is moved away by means of the bolt grip RG from the projection VS, then pressure in hose piece SC, whose wall WD is distorted back from pressure, causes the adjusting device SV to jump into the open position of shutoff device SE depicted in FIG. 1b.

Bolt RL is held in a setting that matches the closed setting in a known manner by a spring piece which is not depicted on its own. Bolt RL in addition is provided with a suitably configured slant surface. In combination with an appropriately configured opposing surface on projection VS, this slant surface makes possible motion of the adjusting device SV, while shifting bolt RL, into the closed setting. If this setting has been attained, bolt RL is pressed back by the spring element into the closed setting.

Hose piece SC shutoff device SE makes a transition at its two ends into shutoff device entry SY or into the shutoff device exit SZ of shutoff device housing SH. The side placed at SY matches the insertion side of a guide catheter and is designated as the proximal side of the shutoff device. The side facing the blood vessel at SZ is that of the shutoff device placed distally.

Figure 2:
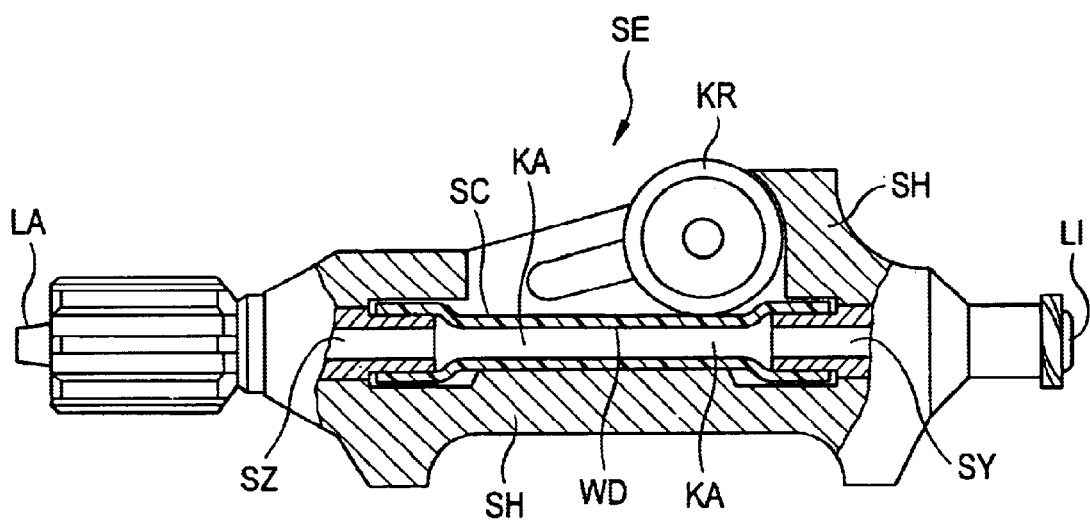
FIG. 2 is a cross-sectional view of a shutoff device with standardized plug junctions placed at its inlet and its outlet, in thus case Luer attachments.

FIG. 2 shows an embodiment of shutoff device SE with two Luer attachments placed on the shutoff device entry SY and on shutoff device exit SZ, in the example depicted a Luer internal wedge LI on shutoff device entry SY and a Luer external wedge LA with a hasp safety mechanism on the shutoff device exit SZ. This shutoff device SE is able to be simply fitted between customary insertion valves and guide catheters, and can be easily fabricated using injection molding technology. The insertion valve's attachment piece can be attached to the Luer internal wedge KI, and the guide catheter's attachment piece correspondingly to the Luer external wedge.

As an adjusting device SV, the shutoff device SE has a grip roller KR, which, with its axis, can be rolled in a fluted guide placed at an angle to the axis of hose piece SC, and held in the selected setting through friction. This embodiment shape resembles known grip rollers which have proven themselves in throttling or closing infusion lines.

Figure 3A:
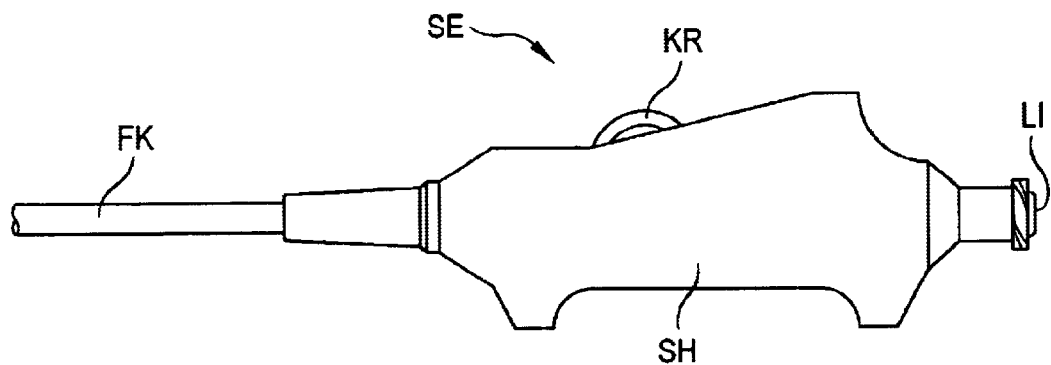
FIGS. 3a, 3b and 3c illustrate the essential method of placement of the shutoff device in the particular insertion system according to the invention.
Figure 3B:
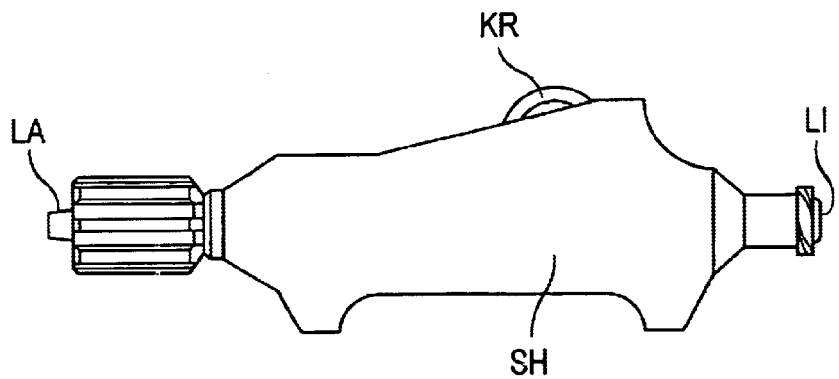
Figure 3C:
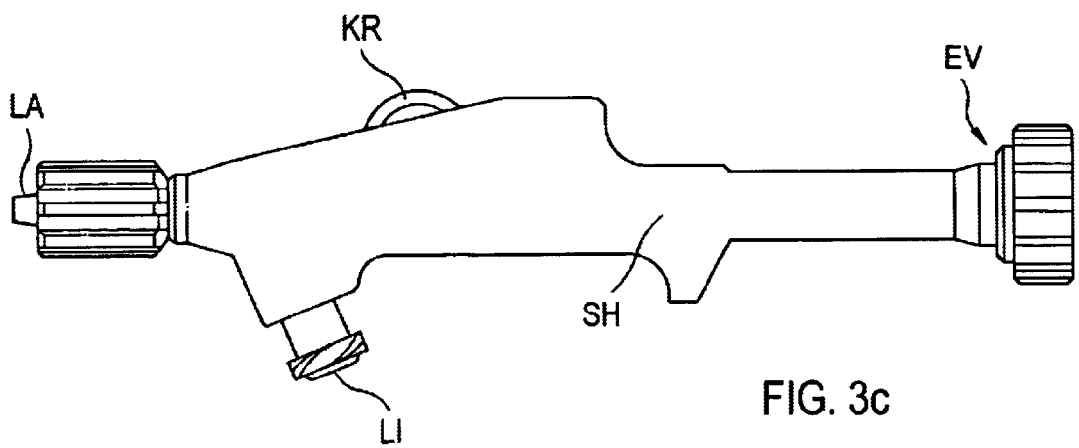

Other options for realizing an invention-specific shutoff device SE consist in such measures as a pliers mechanism or in a configuration in which a band laid about the hose piece SC in the plane of clamping cross section SQ outside about the hose wall can tie off hose piece SC by pulling its ends apart. Such embodiment forms, which are claimed here only generally, likewise represent implementations of the invention concept as do all equivalent configurations. FIGS. 3a to 3c are schematic representations of three essential usage types of the shutoff device SE, in which it can carry out its function in solving the problem posed. As shown in FIG. 3a, it can, for example, be fitted into the shaft of guide catheter FK. One more attachment with a Luer attachment LI is provided on the proximal end, which for example, can be attached to the insertion valve (not shown).

The second option for configuring the shutoff device SE as a supplementary piece to be coupled in by means of Luer attachments between an insertion valve EV (not shown) and a guide catheter FK, supplementing the customary insertion instrument set, is already described above; the corresponding illustration for this is found in FIG. 3b.

The third significant embodiment option is shown in FIG. 3c. In this case the shutoff device SE is placed in the insertion valve shaft of insertion valve EV. It is advantageous if the interval between the sealing ring of insertion valve EV and the hose piece SC of shutoff device SE is greater than the length of the head piece of the treatment catheter to be inserted. In this case, "head piece" is meant to denote that section of the treatment catheter which extends from the catheter tip to the transition to the main shaft of the catheter, i.e., in the adjacent area of cross sectional exterior shape that remains the same of the main shaft. FIG. 3c also shows a side channel with a lumen LI, into which, for example, a syringe can be inserted to draw a sterile, clear liquid into the lock chamber.

The sealing ring of insertion valve EV and the shutoff device SE somewhat carry out the function of two lock gates at the ends of a lock chamber in channel KA. These functions can be taken over by the sealing ring and the shutoff device SE, if a guide wire is in channel KA. The insertion valve EV thus includes a first shutoff device and the shutoff device according to the invention presents a second shutoff device for the insertion system.

There has thus been shown and described a novel insertion system for use in entering the lumen of a blood vessel which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. An insertion system for use when entering the lumen of a blood vessel, for inserting and changing a treatment catheter having a main shaft of substantially constant cross-section and a head piece section which extends from a tip of the treatment catheter to said main shaft, said system comprising, in combination:
    (a) a guide catheter having a guide catheter channel;
    (b) an insertion channel which extends from a proximal end to a distal end that is connected to the guide catheter channel;
    (c) an insertion valve disposed at said proximal end of the insertion channel, the insertion valve having an insertion opening for inserting the treatment catheter and having a manually controllable first shutoff device for opening and closing the insertion opening and for adapting the insertion opening to the diameter of the main shaft; and (d) a manually controllable second shutoff device, disposed in said insertion channel at a location distal to said insertion opening, for closing the insertion channel at said distal location;
   wherein a section of the insertion channel between the first and the second shutoff device forms a lock chamber so that, by suitable closing, adapting and opening of the first and second shutoff devices, respectively, the treatment catheter may be inserted into the lock chamber and into the guide catheter and thereafter changed without any outflow of blood out of the insertion valve, the lock chamber having a length greater than that of the head piece section of the treatment catheter.

2. Insertion system according to claim 1, wherein the insertion channel between the insertion opening of insertion valve and the guide catheter channel has a pipe-shaped hose piece with a wall which can be shaped by means of an adjustment device of the second shutoff device in such a way that the interior channel cross section of this hose piece can be closed liquid-tight.

3. Insertion system according to claim 2, wherein the hose piece has an interior cross section that remains essentially constant throughout its length, except when closed by the attachment device.

4. Insertion system according to claim 1, wherein the second shutoff device is disposed in a separate housing, which can be fitted in between a proximal end of the guide catheter channel and a distal exit of the insertion valve.

5. Insertion system according to claim 4, wherein the second shutoff device comprises its own attachment elements, by means of which the second shutoff device can be connected with corresponding attachment devices of at least one of the insertion valve and guide catheter, respectively.

6. Insertion system according to claim 1, wherein the second shutoff device is disposed in a separate housing from that of the insertion valve.

7. Insertion system according to claim 2, wherein a lumen of a first side channel is connected with the insertion channel proximally near the second shutoff device.

8. Insertion system according to claim 1, wherein a lumen of a second side channel is connected with the insertion channel distally near the insertion opening of the insertion valve.

9. Insertion system according to claim 1, wherein the second shutoff device is inserted in a the insertion channel at a close distance from the proximal entrance of the guide catheter channel.

10. Insertion system according to claim 1, wherein the second shutoff device is placed adjacent to the distal end of a channel of the insertion valve.

11. Insertion system according to claim 10, wherein the second shutoff device is securely connected to the distal end of the insertion valve.

12. Insertion system according to claim 10, wherein the second shutoff device forms a single piece with the distal end of the insertion valve.

13. The insertion system according to claim 1, wherein the second shutoff device is inserted in the insertion channel at a close distance from the distal exit of the insertion valve.

* * * * *